United States Patent [19]

Schaus et al.

[11] Patent Number: 5,457,121
[45] Date of Patent: Oct. 10, 1995

[54] CIS-HEXAHYDRO-5-(1,2,3,4-TETRAHYDRO-2-NAPHTHALENYL)PYRROLO<3,4-C>PYRROLES AS INHIBITORS OF SEROTONIN REUPTAKE

[75] Inventors: John M. Schaus, Zionsville; Robert D. Titus, Indianapolis, both of Ind.

[73] Assignee: Eli Lilly and Company, Indianapolis, Ind.

[21] Appl. No.: 300,299

[22] Filed: Sep. 2, 1994

[51] Int. Cl.⁶ ............................ A61K 31/40; C07D 487/02
[52] U.S. Cl. ............................................. 514/412; 548/453
[58] Field of Search .............................. 548/453; 514/412

[56] References Cited

U.S. PATENT DOCUMENTS

| | | | |
|---|---|---|---|
| 4,308,226 | 12/1981 | Seiler | 424/246 |
| 4,845,221 | 7/1989 | Stack et al. | 544/295 |
| 4,880,802 | 11/1989 | Schohe et al. | 514/222.2 |
| 5,026,707 | 6/1991 | Nixon et al. | 514/255 |

FOREIGN PATENT DOCUMENTS

| | | |
|---|---|---|
| 2247887 | 3/1992 | United Kingdom . |
| WO87/02035 | 4/1987 | WIPO . |
| WO 92/06967 | 4/1992 | WIPO . |

OTHER PUBLICATIONS

Nichols, et al., *J. Med. Chem.*, 33, 703–710 (1990) Month of publication not provided.
Hibert, et al., *Eur. J. Med. Chem.*, 24, 31–37 (1989) Month of publication not provided.
Singh, *Arzneim.–Forsch./Drug Res.*, 36, 1437–1439 (1986) Month of publication not provided.
Bateman, *Br. J. clin. Pharmac.*, 20, 339–344 (1985) Month of publication not provided.
Arvidsson, et al., *J. Med. Chem.*, 27, 45–51 (1984) Month of publication not provided.
Hacksell, et al., *J. Med. Chem.*, 22, 1469–1475 (1979) Month of publication not provided.
McDermed, et al., *J. Med. Chem.*, 18(4), 362–367 (1975) Month of publication not provided.

*Primary Examiner*—Mukund J. Shah
*Assistant Examiner*—K. L. Wong
*Attorney, Agent, or Firm*—Joseph A. Jones; David E. Boone; Gerald V. Dahling

[57] ABSTRACT

This invention provides ring-substituted cis-hexahydro-5-(1, 2,3,4-tetrahydro-2-naphthalenyl)pyrrolo< 3,4-c>pyrroles which are selective inhibitors of serotonin reuptake.

22 Claims, No Drawings

CIS-HEXAHYDRO-5-(1,2,3,4-TETRAHYDRO-2-NAPHTHALENYL)PYRROLO<3,4-C>PYRROLES AS INHIBITORS OF SEROTONIN REUPTAKE

BACKGROUND OF THE INVENTION

During the past two decades, the relationship between neuronal monoamines in the brain and a variety of diseases and conditions has been appreciated and investigated. The discovery of selective monoamine reuptake inhibitors has provided the medical community with exciting new tools with the potential for treatment of several physiological and psychological disorders. Reuptake inhibitors increase the levels of endogenous monoamines by inhibiting the neuronal mechanism for recovering the monoamine from the synapse without interfering with the neuronal receptors. If the reuptake inhibitor is selective for a particular monoamine, undesirable side-effects from the therapy can be reduced.

Fluoxetine, a selective inhibitor of serotonin reuptake, has gained wide acceptance as a therapy for the treatment of depression and eating disorders, and is under active investigation for the treatment of other disorders. Similarly, tomoxetine hydrochloride [(-)-N-methyl-3-(2-methylphenoxy) propanamine hydrochloride] is a selective inhibitor of norepinephrine uptake being investigated clinically for the treatment of urinary incontinence. These compounds are among many taught in U.S. Pat. Nos. 4,018,895, 4,194,009, 4,314,081 and 5,026,707 as being potent inhibitors of the uptake of various physiologically active monoamines, including serotonin, norepinephrine and dopamine.

The present invention provides novel compounds which are potent, selective inhibitors of serotonin.

SUMMARY OF THE INVENTION

The present invention provides novel ring-substituted cis-hexahydro-5-(1,2,3,4-tetrahydro-2-naphthalenyl)pyrrolo< 3,4-c>pyrroles of the formula

I in which
R is hydrogen, methyl or benzyl;
$R^1$ is hydrogen or methyl;
$R^2$ is selected from the group consisting of hydrogen, halo, $C_1$–$C_3$ alkoxy, $C_1$–$C_3$ alkylthio, $C_1$–$C_3$ alkyl and hydroxy;
$R^3$ is selected from the group consisting of hydrogen and halo;
$R^4$ is selected from the group consisting of hydrogen, halo, $C_1$–$C_3$ alkoxy, $C_1$–$C_3$ alkylthio, $C_1$–$C_3$ alkyl and hydroxy;
$R^5$ is selected from the group consisting of hydrogen, halo, $C_1$–$C_3$ alkyl, $C_1$–$C_3$ alkoxy, $C_1$–$C_3$ acyl, fluorosubstituted $C_2$–$C_3$ acyl, fluorosubstituted $C_1$–$C_3$ alkyl, cyano, carboxamido, carboxyl and $C_1$–$C_3$ hydroxyalkyl; all subject to the following provisos:

(a) $R^5$ may be other than hydrogen only when $R^2$ is other than hydrogen;
(b) $R^3$ may be halo only when $R^4$ is other than hydrogen; and pharmaceutically acceptable acid addition salts thereof. This invention also provides a pharmaceutical formulation which comprises, in association with a pharmaceutically acceptable carrier, diluent or excipient, a compound of Formula I.

A further embodiment of the invention is a method for selectively inhibiting the reuptake of serotonin. More particularly, further embodiments are methods for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism or trichotillomania. Any of these methods employ a compound of Formula I.

DETAILED DESCRIPTION OF THE INVENTION

In the above formula, the term "$C_1$–$C_3$ alkyl" means a straight or branched alkyl chain bearing from one to three carbon atoms. Such $C_1$–$C_3$ alkyl groups are methyl, ethyl, propyl and isopropyl.

The term "$C_1$–$C_3$ alkoxy" means any of methoxy, ethoxy, n-propoxy and isopropoxy.

The term "halo" means any of fluoro, chloro, bromo or iodo.

The term "$C_1$–$C_3$ acyl" means any of formyl, acetyl and propionyl.

The term "fluorosubstituted $C_1$–$C_3$ acyl" means mono-, di- or trifluorosubstituted acetyl, or mono-, di-, tri-, tetra- or pentafluorosubstituted propionyl. Specific examples are fluoroacetyl, trifluoroacetyl, β,β,β-trifluoropropionyl, -β fluoropropionyl, β,β-fluoropropionyl and the like.

The term "fluorosubstituted $C_1$–$C_3$ alkyl" means mono-, di- or trifluoromethyl, or mono-, di-, tri-, tetra- or pentafluoroethyl, or mono-, di-, tri-, tetra-, penta-, hexa- or heptafluoropropyl or isopropyl. Specific examples are fluoromethyl, trifluoromethyl, 2,2,2-trifluoroethyl, 3-fluoropropyl, 1-methyl-2-fluoroethyl, heptafluoro-n-propyl and the like.

The term "$C_1$–$C_3$ alkylthio" means any of methylthio, ethylthio, n-propylthio and isopropylthio.

The term "$C_1$–$C_3$ hydroxyalkyl" means a $C_1$–$C_3$ alkyl having a hydroxyl group. Examples are hydroxymethyl, 2-hydroxyethyl, 3-hydroxypropyl and the like.

While all of the compounds of the present invention are useful for treating a variety of disorders which have been linked to decreased neurotransmission of serotonin in mammals (or as intermediates to such compounds), certain of the compounds are preferred. Thus, when $R^4$ is other than hydrogen, $R^1$ is preferably methyl, and when $R^2$ is other than hydrogen, $R^1$ preferably is hydrogen.

When $R^2$ is other than hydrogen, it preferably is alkoxy or halo, and, more preferably, is methoxy or chloro. Most preferably, $R^2$ when not hydrogen, is methoxy It is also preferred that, when $R^5$ is other than hydrogen, it preferably is halo, and, most preferably, bromo.

When $R^4$ is other than hydrogen, it preferably is halo, and, most preferably, chloro.

When $R^1$ is hydrogen, the compounds of the present invention possess an asymmetric carbon labelled with an asterisk in the following formula:

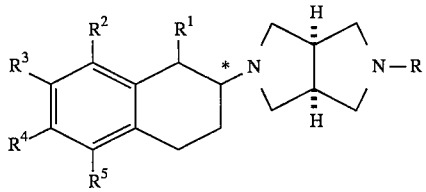

Each of the compounds exists as its individual d- and l-stereoisomers as well as the racemic mixture of such isomers. Additionally, when $R^1$ is methyl, a second asymmetric carbon located at the carbon bearing the $R^1$ substituent is present, giving rise to a class of diastereomers. The compounds of the present invention include not only the diastereomeric or dl-racemates but also their respective optically active diastereomers or d- and l-isomers.

As mentioned hereinabove, the invention includes pharmaceutically acceptable acid addition salts of the compounds defined by the above formula. Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, -β hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, hydrobromic acid or maleic acid. The maleic acid salts are most preferred.

The following compounds further illustrate compounds contemplated within the scope of this invention:
cis-hexahydro-5-(cis-1-methyl-1,2,3,4-tetrahydro-2-naphthalenyl)pyrrolo< 3,4-c>pyrrole;
cis-hexahydro-2-methyl-5-(1,2,3,4-tetrahydro-2-naphthalenyl)-pyrrolo< 3,4-c>pyrrole;
cis-hexahydro-5-(1,2,3,4-tetrahydro-8-methylthio-2-naphthalenyl)pyrrolo< 3,4-c>pyrrole;
cis-hexahydro-2-methyl-5-(1,2,3,4-tetrahydro-8-ethylthio-2-naphthalenyl)pyrrolo< 3,4-c>pyrrole;
cis-hexahydro-5-(cis-1-methyl-1,2,3,4-tetrahydro-6-ethyl-2-naphthalenyl)pyrrolo< 3,4-c>pyrrole;
cis-hexahydro-2-methyl-5-(cis-1-methyl-1,2,3,4-tetrahydro-6-ethoxy- 2-naphthalenyl)pyrrolo<3,4-c>pyrrole;
cis-hexahydro-2-benzyl-5-(1,2,3,4-tetrahydro-8-hydroxy-2-naphthalenyl)pyrrolo< 3,4-c>pyrrole;
cis-hexahydro-5-(cis-1-methyl-1,2,3,4-tetrahydro-6-n-propyl- 2-naphthalenyl)pyrrolo<3,4-c>pyrrole;
cis-hexahydro-5-(1,2,3,4-tetrahydro-5-trifluoromethyl-8-iodo- 2-naphthalenyl)pyrrolo<3,4-c>pyrrole;
cis-hexahydro-2-methyl-5-(1,2,3,4-tetrahydro-5-acetyl-8-chloro- 2-naphthalenyl)pyrrolo<3,4-c>pyrrole;
cis-hexahydro-5-(1,2,3,4-tetrahydro-5-fluoroacetyl-8-methylthio- 2-naphthalenyl)pyrrolo<3,4-c>pyrrole;
cis-hexahydro-2-methyl-5-(1,2,3,4-tetrahydro-8-n-propyl-2-naphthalenyl)pyrrolo< 3,4-c>pyrrole;
cis-hexahydro-5-(1,2,3,4-tetrahydro-6-ethylthio-2-naphthalenyl)pyrrolo< 3,4-c>pyrrole;
cis-hexahydro-2-methyl-5-(1,2,3,4-tetrahydro-6-isopropyl-2-naphthalenyl)pyrrolo< 3,4-c>pyrrole and the like.

The compounds of the present invention may be prepared by procedures well known to those of ordinary skill in the art. The compounds preferably are synthesized by preparation of selected 2-tetralones and cis-hexahydropyrrolo<3,4-c>pyrroles. The 2-tetralone then is reductively aminated with a cis-hexahydropyrrolo<3,4-c>pyrrole to produce selected compounds of this invention. Other compounds of this invention are available by modifications of the ring substituents following the reductive amination step. Schemes for these reactions are as follows:

A. Synthesis of Tetralones

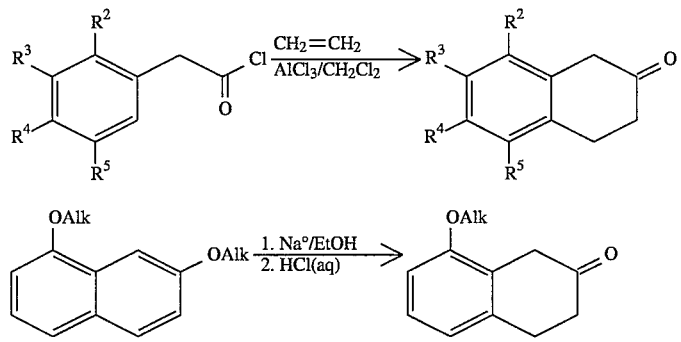

1.

2.

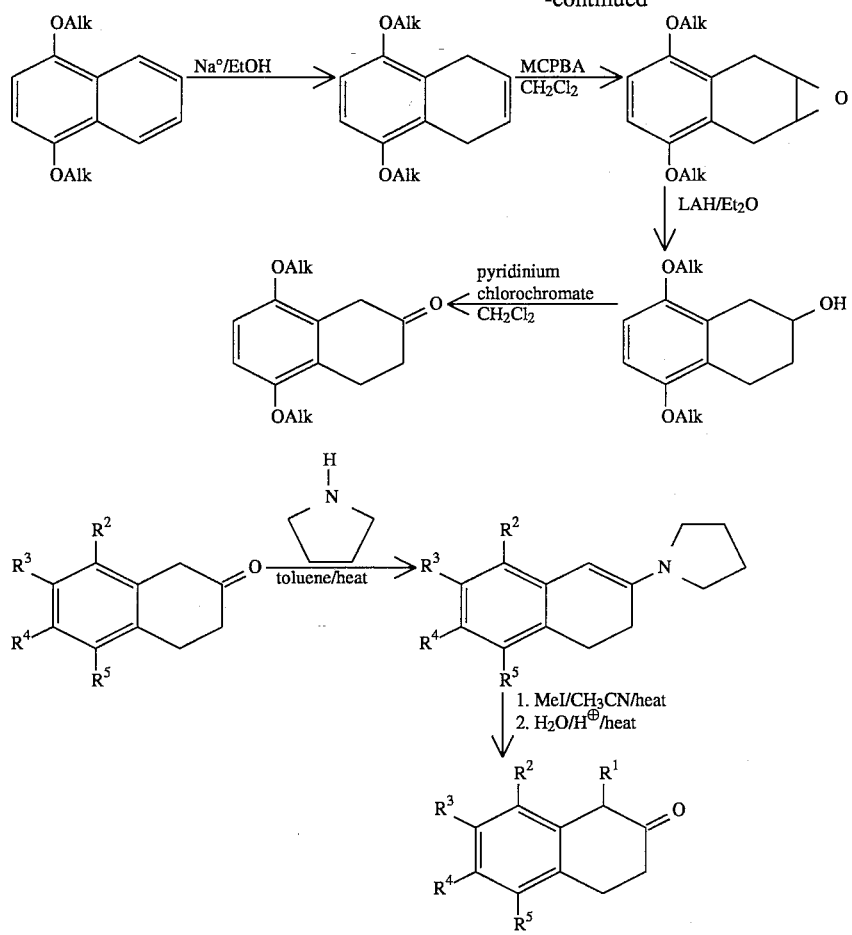
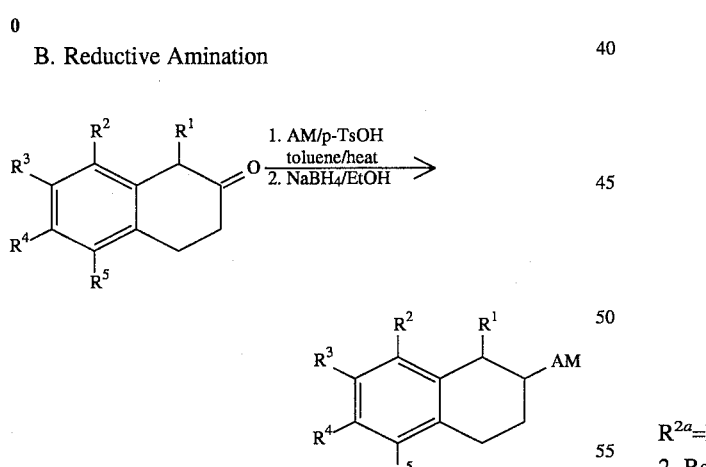
AM = an optionally substituted cis-hexahydropyrrolo-<3,4-c>pyrrole
C. Modification of Aromatic Ring Substituents
1. Bromination
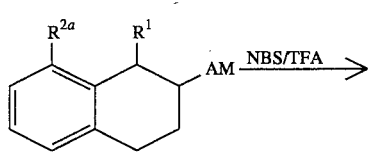
-continued
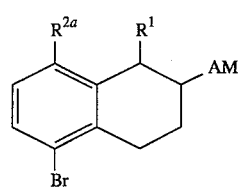
$R^{2a}$=halo, $C_1$–$C_3$ alkoxy, $C_1$–$C_3$ alkylthio or $C_1$–$C_3$ alkyl
2. Replacement of Bromo Ring Substituent
a) via lithiation
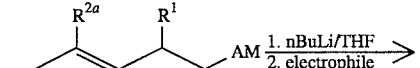

-continued

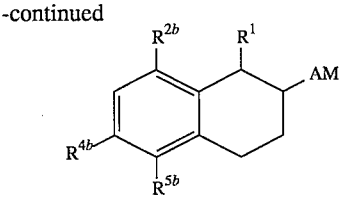

When $R^{2a}$=bromo:

| Electrophile | Product | Allowed Substituent |
|---|---|---|
| Alkyl-S-S-Alkyl | $R^{2b}$ = -S-Alkyl | $R^{5a-b}$ = H, alkoxy |
| When $R^{4a}$ = bromo: | | |
| Alkyl-S-S-Alk | $R^{4b}$ = -S-Alkyl | — |
| When $R^{5a}$ = bromo: | | |
| | ($R^{5b}$) | |
| $FOClO_2$ | F | $R^{2a-b}$ = alkoxy, alkylthio, alkyl |
| NCS | Cl | $R^{2a-b}$ = alkoxy, alkylthio, alkyl |
| $I_2$ | I | $R^{2a-b}$ = alkoxy, alkylthio, alkyl |
| $C_1$–$C_3$ acyl-$NMe_2$ | $C_1$–$C_3$ acyl | $R^{2a-b}$ = alkoxy, alkylthio, alkyl |
| $(C_1$–$C_3$ acyl$)_2$O | $C_1$–$C_3$ acyl | $R^{2a-b}$ = alkoxy, alkylthio, alkyl |
| $(C_1$–$C_3$ F-subst. acyl$)_2$O | $C_1$–$C_3$ F-subst. acyl | $R^{2a-b}$ = alkoxy, alkylthio, alkyl |
| Trimethylsilyliso- cyanate | $CONH_2$ | $R^{2a-b}$ = alkoxy, alkylthio, alkyl |
| $CO_2$ | $CO_2H$ | $R^{2a-b}$ = alkoxy, alkylthio, alkyl | b) via Nucleophilic Aromatic Substitution

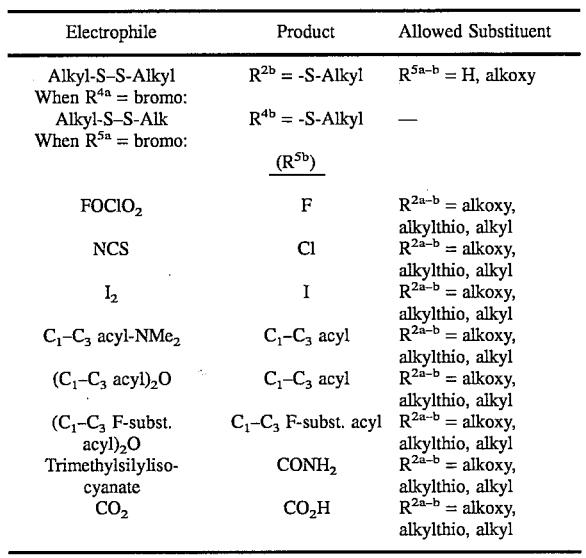

3. Formation of 5-(Fluorosubstituted Alkyl) Compounds

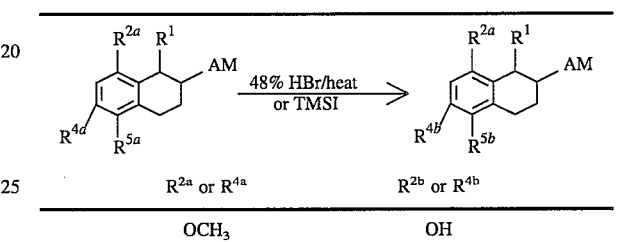

| $R^{5a}$ | $R^{5b}$ |
|---|---|
| $CH_2OH$ | $CH_2F$ |
| CHO | $CHF_2$ |
| $CO_2H$ | $CF_3$ |

(DAST = Diethylaminosulfur trifluoride)
$R^{2a}$ = halo, alkoxy, alkylthio or alkyl.

4. Formation of 6- or 8-Hydroxy Compounds

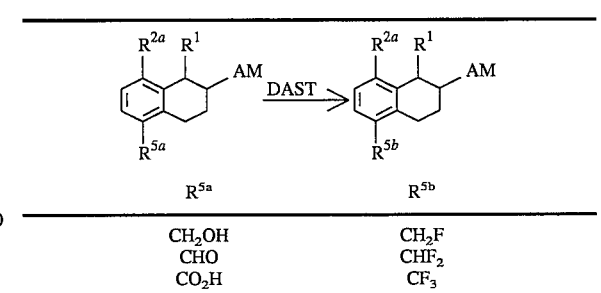

| $R^{2a}$ or $R^{4a}$ | $R^{2b}$ or $R^{4b}$ |
|---|---|
| $OCH_3$ | OH |

TMSI = Trimethylsilyl iodide

D. Synthesis of cis-hexahydropyrrolo<3,4-C>pyrroles

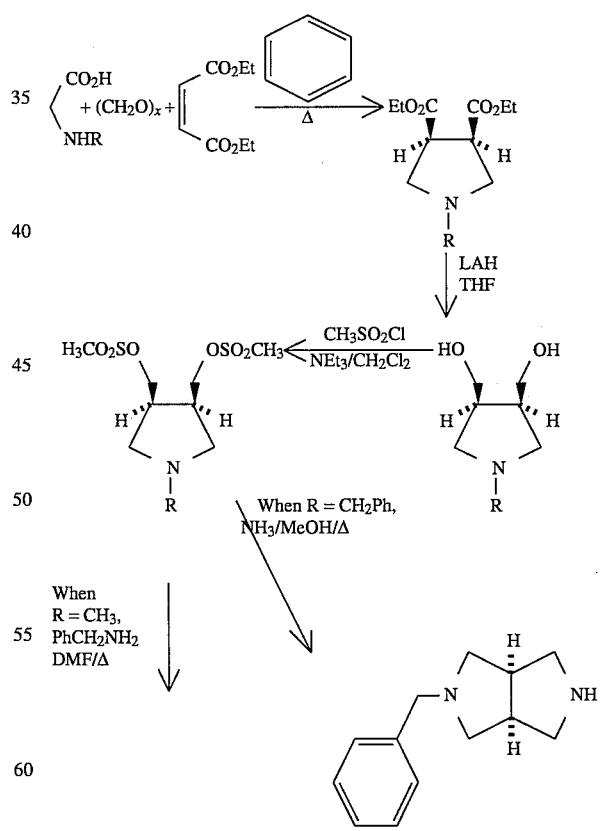

-continued

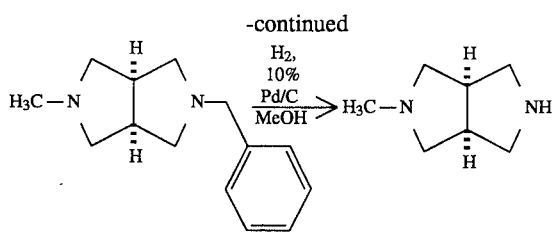

As illustrated above, the tetralones represent the intermediates which, when reductively aminated with the appropriate cis-hexahydropyrrolo<3,4-c>pyrrole, result in compounds of this invention or compounds that have the core structure of the compounds of this invention.

The tetralones are available by any of a wide range of recognized methods. For example, they can be produced by a Friedel-Crafts reaction of an appropriately ring-substituted phenylacetyl chloride with ethylene in the presence of aluminum chloride.

A 1,7-dialkoxynaphthalene can be reduced with sodium and the resultant enol ether hydrolyzed to the corresponding monoalkoxytetralone.

Another method for obtaining a specific tetralone is via 1,4-dialkoxynaphthalene. The naphthalene is reduced with sodium to give 1,4-dihydro-5,8-dialkoxynaphthalene, and the latter is oxidized with m-chloroperbenzoic acid to the corresponding epoxide. The epoxide is reduced with lithium aluminum hydride (LAH), and the resulting alcohol oxidized to the desired tetralone using pyridinium chlorochromate.

When $R^1$ in the compounds of this invention is methyl, the methyl-substituted tetralone can be prepared from the unsubstituted tetralone. The tetralone is first treated with pyrrolidine to produce the corresponding 1,2-dihydro-3-pyrrolidinylnaphthalene. The latter, upon treatment with iodomethane followed by acid hydrolysis, gives the desired 1-methyl- 2-tetralone.

The 2-methyl- and 2-benzyl-cis-hexahydropyrrolo<3,4-c>pyrroles are conveniently prepared by the condensation of the appropriately N-substituted glycine with paraformaldehyde which immediately undergoes a cycloaddition with dimethyl maleate to give the corresponding N-substituted-cis-3,4pyrrolidinedicarboxylic acid dimethyl ester. The diester is reduced with lithium aluminum hydride to the corresponding diol which is then converted to the dimesylate by reaction with methanesulfonyl chloride in the presence of triethylamine.

When R is methyl, the dimesylate can be reacted with benzylamine at reflux to give cis-hexahydro-2-methyl-5benzylpyrrolo< 3,4-c>pyrrole, followed by debenzylation under catalytic hydrogenation conditions employing 10% palladium on carbon, giving cis-hexahydro-2-methylpyrrolo-<3,4-c>pyrrole. Alternatively, the dimesylate can be reacted with anhydrous ammonia in methanol at 200° C. in a pressure vessel to give the same compound.

When R is benzyl, the dimesylate is reacted with anhydrous ammonia in methanol at 200° C. in a pressure vessel to give cis-hexahydro-2-benzylpyrrolo<3,4-c>pyrrole.

The tetralone can be converted to a compound of this invention or to one useful as an intermediate to a compound of this invention by reductive amination with a cis-hexahydropyrrolo< 3,4-c>pyrrole. The tetralone is first reacted with a cis-hexahydropyrrolo<3,4-c>pyrrole to form the corresponding enamine which is then reduced with sodium borohydride to the tetrahydronaphthalene.

Other of the compounds of this invention are available, first by incorporation and then by replacement of a ring substituent on the tetrahydronaphthalene moiety. A compound of this invention having a compatible substituent in the 8-position can be treated with N-bromosuccinimide to produce the corresponding 5-bromo compound.

A tetrahydronaphthalene having a bromo substituent, whether in the 5-, 6- or 8-position, is useful to produce other compounds of this invention via formation of the corresponding organolithium using n-butyllithium. The reactive organolithium intermediate can be trapped with a wide variety of electrophiles to produce compounds of this invention. Thus, treatment of the organolithium with a dialkyl disulfide produces an alkylthio substituent, with $FOClO_2$ a fluoro substituent, with N-chlorosuccinimide a chloro substituent, with iodine an iodo substituent, with N,N-dimethylformamide or an acyl anhydride an acyl substituent, with a fluoro-substituted acyl anhydride a fluoro-substituted acyl substituent, with trimethylsilyl isocyanate a carboxamido substituent and with carbon dioxide a carboxyl substituent.

The 5-bromotetrahydronaphthalene is converted to its corresponding cyano compound by treatment with cuprous cyanide at elevated temperature.

Compounds of this invention in which the 5-substituent is a fluoro-substituted alkyl group are available by treatment of the corresponding alcohol, aldehyde or carboxylic acid with diethylaminosulfur trifluoride (DAST).

Compounds of this invention in which the ring substituent is hydroxy are available from the corresponding alkoxy compound by treatment with 48% hydrobromic acid or trimethylsilyl iodide.

Compounds of this invention in which the R substituent is hydrogen are available by hydrogenation of the corresponding N-benzyl intermediate over 10% palladium on carbon.

The optically active isomers of the racemates of this invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization.

The compounds employed as starting materials in the synthesis of the compounds of this invention are well known and readily synthesized by standard procedures commonly employed by those of ordinary skill in the art.

The pharmaceutically acceptable acid addition salts of the invention are typically formed by reacting a cis-hexahydro-5-(1,2,3,4-tetrahydro-2-naphthalenyl)pyrrolo< 3,4-c>pyrrole of this invention with an equimolar or excess amount of acid. The reactants are generally combined in a mutual solvent such as ethanol, and the salt normally precipitates out of solution within about 1 hour to 10 days, and can be isolated by filtration.

The following examples further illustrate the compounds of the present invention and methods for their synthesis. The examples are not intended to be limiting to the scope of the invention in any respect and should not be so construed.

Unless otherwise noted, the NMR data appearing in the following examples refers to the free bases of the subject compounds.

Preparation of cis-hexahydropyrrolo<3,4-c>pyrroles

A. 1-methyl-cis-3,4-pyrrolidinedicarboxylic acid dimethyl ester

A mixture of 89.0 gm (1.0 mole) N-methylglycine, 60.0 gm (2.0 mole) paraformaldehyde and 144 gm (1.0 mole) dimethyl maleate in 1 L of benzene were heated to reflux with constant water removal for about 5 hours. The reaction mixture was cooled to ambient and allowed to stand over night. The solution was decanted from the solid and the solid was washed with diethyl ether. The combined organic phases were extracted with 10% hydrochloric acid and then this aqueous phase was made basic with concentrated ammonium hydroxide. The now basic aqueous phase was extracted with dichloromethane and the organic extracts were then dried over sodium sulfate and concentrated in vacuo to give a yellow liquid. This material was fractionated through a Vigreaux column to give 74.25 gm of the desired compound, b.p.=119°–123° C. (8 mm Hg).

IR (CHCl$_3$): 1740 cm$^{-1}$
$^{13}$C-NMR (CDCl$_3$): 172.89, 58.23, 51.88, 45.80, 41.84.
MS: 201(35), 186(10), 170(30), 154(5), 142(30), 115(45), 82 (100), 57 (100) .

Analysis, calculated for C$_9$H$_{15}$NO$_4$: Theory: C , 53.72; H, 7.51; N, 6.96. Found: C, 53.47; H, 7.60; N, 6.93.

B. 1-methyl-cis-3,4-di (hydroxymethyl) pyrrolidine

To a suspension of 3.8 gm (100 mMol) lithium aluminum hydride in 200 mL tetrahydrofuran were added dropwise a solution of 10.0 gm (50.0 mMol) 1-methyl-cis-3,4-pyrrolidinedicarboxylic acid dimethyl ester in 50.0 mL tetrahydrofuran. The reaction mixture was stirred at ambient for about 1 hour and was then quenched by the sequential addition of 3.8 mL water, 3.8 mL 15% aqueous sodium hydroxide solution and 11.4 mL of water. The resultant mixture was stirred at ambient for 20 hours. At this point the suspension was filtered through a bed of Celite and the filter cake was washed with tetrahydrofuran. The combined liltrates were concentrated in vacuo to give 6.7 gm of the desired compound as a light yellow oil.

IR (CHCl$_3$): 3380 cm$^{-1}$
$^{13}$C-NMR(CDCl$_3$): 61.93, 58.95, 42.21, 42.06.
MS: 145(40), 144(35), 126(20), 114(20), 96(15), 87(25), 82 (50), 57 (100).

C. 1-methyl-cis-3,4-di(methanesulfonyloxymethyl)pyrrolidine

To an ice cooled solution of 6.2 gm (43 mMol) 1-methyl-cis- 3,4-di(hydroxymethyl) pyrrolidine and 14.5 gm(143 mMol ) triethylamine in 200 mL dichloromethane was added a solution of 14.7 gm (129 mMol) methanesulfonyl chloride in 20 mL dichloromethane. Once this addition was complete the reaction mixture was stirred for 15 minutes at 0° C. and then for 1.5 hours at ambient. The reaction mixture was then quenched with dilute aqueous sodium hydroxide solution and then was extracted with dichloromethane. The organic phase was dried over sodium sulfate and then concentrated in vacuo to give 9.6 gm of the desired compound as an orange oil.

MS: 301(4), 300(3), 206(30), 110(15), 86(25), 67(30), 57 (100).

D. cis-hexahydro-2-methyl-5-benzylpyrrolo<3,4-c>pyrrole

A solution of 13 gm (43 mMol) 1-methyl-cis-3,4-di(methanesulfonyloxymethyl)pyrrolidine in 100 mL benzylamine were heated to reflux with the benzylamine being slowly distilled off. After 5 hours the reaction mixture was poured into dilute aqueous sodium hydroxide solution and extracted with 3:1 chloroform:isopropanol. The organic phase was dried over sodium sulfate and then concentrated in vacuo to give a yellow oil. Most of the benzylamine remaining in this oil was removed by distillation at atmospheric pressure and then the remaining liquid was fractionated under vacuum to give 7.0 gm of the desired product, b.p.=148°–165° C. (8 mm Hg).

NMR(CDCl$_3$): 7.3–7.0 (m, 5H), 3.5 (s, 2H), 2.8–1.9 (m, 10H), 2.3 (s, 3H).

MS: 296(10), 263(40), 262(100), 248(15), 216(50), 195(5), 150(75).

E. cis-hexahydro-2-methylpyrrolo<3,4-c>pyrrole (1) To a solution of 3.5 gm (16.2 mMol) cis-hexahydro-2-methyl-5-benzylpyrrolo<3,4-c>pyrrole in 150 mL ethanol were added 2.5 gm 10% palladium on carbon. The reaction mixture was hydrogenated at 50 p.s.i. and 60° C. for 2 hours. The reaction mixture was then filtered through Celite and the filter pad rinsed with methanol. The combined liltrates were concentrated in vacuo to give 1.59 gm of the desired compound as a cloudy, white oil.

(2) Alternatively, the title compound was prepared by adding 100 mL liquid ammonia to a solution of 1.02 gm (3.3 mMol) N-methyl-cis-3,4-di(methanesulfonyloxymethyl)pyrrolidine in 100 mL methanol and the mixture was heated in a sealed reactor at 200° C. for 5 hours. The reaction mixture was then concentrated in vacuo to give a tan solid. This solid was dissolved in water and the solution made basic with aqueous sodium hydroxide solution. The aqueous phase was then extracted with 3:1 chloroform:isopropanol and the organic phase dried over sodium sulfate then concentrated in vacuo to give 0.243 gm of the desired product as an orange oil.

NMR(CDCl$_3$): 3.0–2.4 (m, 9H), 2.4–2.2 (m, 2H), 2.3 (s, 3H).

MS: 126(30), 109(15), 96(100), 94(55), 82(80), 68(25), 57(65).

F. cis-hexahydro-2-benzylpyrrolo<3,4-c>pyrrole 47.1 gm N-benzylglycine were subjected to the sequence of reactions described in Preparations A, B, C, E(2) to give 30.6 gm of the title compound as a pale orange oil.

NMR(CDCl$_3$): 7.2 (s, 5H), 2.5 (s, 2H), 3.0–2.4 (m, 8H), 2.4– 2.1 (m, 2H), 1.8 (s, 1H).

EXAMPLE 1

Preparation of cis-hexahydro-2-methyl-5-(1,2,3,4-tetrahydro- 2-naphthalenyl ) pyrrolo<3,4-c>pyrrole dimaleate To a solution of 0.6 gm (4.75 mMol) cis-2-methylhexahydropyrrolo< 3,4-c>pyrrole in 7.0 mL acetonitrile were added 0.11 mL (2.0 mMol) acetic acid followed by 0.12 gm (2 mMol) sodium cyanoborohydride. To this resultant gel were added 0.73 gm (5.0 mMol) 2-tetralone in 5 mL acetonitrile followed by 2.0 gm 3A molecular sieves. The reaction mixture was stirred at ambient for 1.5 hours at which time an additional 0.404 gm (6.4 mMol) sodium cyanoborohydride and 0.315 gm (5.2 mMol) acetic acid were added. The reaction mixture was stirred at ambient for about 18 hours.

The reaction mixture was quenched with 10% hydrochloric acid, filtered through a pad of Celite and the filtrate extracted with methylene chloride. The remaining aqueous phase was made basic with aqueous sodium hydroxide and extracted with 3:1 chloroform:isopropanol. The organic phase was dried over sodium sulfate and concentrated in vacuo to give 0.204 gm of an orange oil.

MS(FD): 256(100), 257(30).

The resultant oil was dissolved in 10 mL 1:1 dichloromethane:diethyl ether and to this solution was added a saturated solution of maleic acid in diethyl ether. The colorless precipitate which formed was washed with diethyl ether and then recrystallized from methanol to give 0.196 gm of the title compound as colorless crystals, m.p.=189.5°–190.5° C.

NMR(CDCl$_3$): 7.0 (s, 4H), 3.2–2.6 (m, 8H), 2.6–1.9 (m, 9H), 2.3 (s, 3H).

Analysis, calculated for $C_{17}H_{24}N_2 \cdot 2C_4H_4O_4$: Theory: C, 61.46; H, 6.60; N, 5.73. Found: C, 61.76; H, 6.56; N, 5.95.

EXAMPLE 2

Preparation of cis-hexahydro-2-methyl-5-(1,2,3,4-tetrahydro- 8-chloro-2-naphthalenyl)pyrrolo<3,4-c>pyrrole dimaleate A. 8-chloro-2-tetralone A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0 %) of o-chlorophenylacetyl chloride as a transparent, pale yellow, mobile liquid.

NMR($CDCl_3$): 7.5–7.1 (m, 4H), 4.2 (s, 2H).

To a slurry of 46.5 gm (0.348 mole) $AlCl_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane: diethyl ether to give 10.55 gm of the title compound.

NMR($CDCl_3$): 7.5–7.2 (m, 3H), 3.7 (s, 2H), 3.3–3.0 (t, J=7 Hz, 2H), 2.8–2.4 (t, J=7 Hz, 2H).

MS: 180(60), 165(9), 138(100), 117(52), 115(50), 103(48), 89 (20), 76 (25), 74 (18), 63 (30), 57 (9), 52 (28), 51 (20), 42 (6), 39(32).

IR(nujol mull): 2950 $cm^{-1}$, 2927 $cm^{-1}$, 1708 $cm^{-1}$, 1464 $cm^{-1}$, 1450 $cm^{-1}$, 1169 $cm^{-1}$, 1141 $cm^{-1}$.

B. cis-hexahydro-2-methyl-5-(1,2,3,4-tetrahydro-8-chloro-2-naphthalenyl)pyrrolo< 3,4-c>pyrrole dimaleate Using 3.24 gm 8-chloro-2-tetralone and 1.83 gm cis-hexahydro- 2-methylpyrrolo<3,4-c>pyrrole in the method described in Example 1, 3.97 gm of the title compound were obtained as a white powder. m.p.=185.5°–187.5° C. (methanol/ethanol).

NMR ($CDCl_3$): 7.2–6.8 (m, 3H), 3.3–2.6 (m, 6H), 2.6–1.9 (m, 11H), 2.3 (s, 3H).

MS: 290 (15), 292(5), 246(30), 248(10), 165(25), 125(30), 96(100), 82 (65 ), 58 (50).

Analysis, calculated for $C_{17}H_{23}N_2Cl \cdot 2C_4H_4O_4$: Theory: C, 57.42; H, 5.97; N, 5.36. Found: C, 57.42; H, 6.10; N, 5.57.

EXAMPLE 3

Preparation of cis-hexahydro-2-methyl-5-(1,2,3,4-tetrahydro- 8-methoxy-2-naphthalenyl)pyrrolo<3,4-c>pyrrole dimaleate A. 8-methoxy-2-tetralone To one liter of acetone were added 50.0 grams (0.31 mole) of 1,7-dihydroxynaphthalene. To the solution then were added 95.0 gm (0.69 mole) of powdered potassium carbonate and 65 mL (0.69 mole) of dimethyl sulfate. The reaction mixture was stirred at reflux under nitrogen for 18 hours. The reaction mixture then was cooled to room temperature and diluted with 2 L of water. The mixture was then extracted with dichloromethane. The organic extracts were combined, washed successively with water and saturated aqueous sodium chloride, dried over sodium sulfate and evaporated in vacuo to give a brown oil. The oil was distilled in vacuo to give 52.51 gm (90.1%) of 1,7-dimethoxynaphthalene as a light orange, transparent oil, b.p.=115°–157° C. (4 mm Hg).

NMR ($CDCl_3$): 7.6–6.9 (m, 5H), 6.7–6.6 (d, J=7.2 Hz, 1H), 3.88 (s, 3H), 3.84 (s, 3H).

To a solution of 52.5 gm (0.279 mole) 1,7-dimethoxynaphthalene in 450 mL ethanol were added 54.4 gm (2.37 mole) of sodium at a rate sufficient to maintain a gentle reflux. Nitrogen was passed through the mixture to purge the system of hydrogen. The mixture was then heated at reflux until all of the sodium was consumed, after which it was cooled to ambient, diluted with 300 mL of water followed by 350 mL of concentrated hydrochloric acid, and then heated on a steam bath for 30 minutes. The mixture was diluted with water until all remaining solids had dissolved and then was cooled to ambient and extracted with diethyl ether. The organic extracts were combined, washed with water, washed with saturated aqueous sodium chloride, dried over sodium sulfate and evaporated in vacuo to give a yellow oil. The oil was dissolved in minimal diethyl ether and added to 250 mL of saturated aqueous sodium bisulfite. The two-phase system was stirred vigorously for 18 hours.

The resulting colorless suspension was filtered and the collected solid was washed with diethyl ether then dried in vacuo. The solid was then added to about 300 mL of 50% aqueous potassium carbonate. Diethyl ether was added and the mixture was stirred vigorously until all of the solid had dissolved. The two-phase mixture was separated and the aqueous portion was extracted with diethyl ether. The combined ether extracts were washed successively with water and saturated aqueous sodium chloride, dried over sodium sulfate and evaporated in vacuo to give 32.8 gm (67%) of the title compound as a colorless, crystalline mass.

NMR ($CDCl_3$): 7.2–7.0 (t, J=7.2 Hz, 1H), 6.8–6.6 (t, J=7.2 Hz, 2H), 3.76 (s, 3H), 3.48 (s, 2H), 3.14–2.92 (t, J=7.2 Hz, 2H) , 2.62–2.46 (t, J=7.2 Hz, 2H ).

B; cis-hexahydro-2-methyl-5-(1,2,3,4-tetrahydro-8-methoxy-2- naphthalenyl)pyrrolo< 3,4-c>pyrrole dimaleate Using 1.45 gm 8-methoxy-2-tetralone and 0.69 gm cis-hexahydro- 2-methylpyrrolo<3,4-c>pyrrole in the method described in Example 1, 0.19 gm of the title compound were obtained as a white powder. m.p.=182°–184° C. dec.(methanol).

NMR ($CDCl_3$): 7.0 (t, J=9 Hz, 1 H), 6.8–6.5 (m, 2H), 3.8 (s, 3H), 3.2–2.9 (m, 2H), 2.9–2.6 (m, 4H), 2.6–1.9 (m, 11H), 2.3 (s, 3H) .

Analysis, calculated for $C_{18}H_{26}N_2O \cdot 2C_4H_4O_4$: Theory: C, 60.22; H, 6.61; N, 5.40. Found: C, 60.02; H, 6.87; N, 5.50.

EXAMPLE 4

Preparation of cis-hexahydro-2-methyl-5-(1,2,3,4-tetrahydro- 8-hydroxy-2-naphthalenyl)pyrrolo<3,4-c>pyrrole dimaleate A solution of 0.30 gm (1.05 mMol) cis-hexahydro-2- methyl- 5-(1,2,3,4-tetrahydro-8-methoxy-2-naphthalenyl)pyrrolo< 3,4-c>pyrrole in 5.0 mL 48% HBr was heated at reflux for 2.0 hours. The reaction mixture was then cooled to ambient and concentrated in vacuo and the residue dissolved in water. This solution was adjusted to pH=9 with aqueous sodium hydroxide and was then extracted with 3:1 chloroform: isopropanol. The organic extract was dried over sodium sulfate and concentrated in vacuo to give 0.312 gm of a brown oil.

The oil was dissolved in 2:5 methanol:dichloromethane and was placed on a flash silica column. The column was then eluted with 2:5 methanol:dichloromethane. Fractions containing the desired product were combined and concentrated in vacuo to give 0.235 gm of a colorless foam.

IR(CHCl$_3$): 3600 cm$^{-1}$, 1580 cm$^{-1}$.

NMR(CDCl$_3$): 9.6 (br s, 1H), 7.9 (t, J=9 Hz, 1H), 7.5 (d, J=9 Hz, 1H), 7.3 (d, J=9 Hz, 1H), 3.4–3.0 (m, 2H), 3.0–2.5 (m, 6H), 2.4 (s, 3H), 2.5–2.0 (m, 4H), 2.0–1.1 (m, 5H).

MS (EI): 272 (100), 273 (20), 228 (40), 147 (30), 125 (20), 96 (55), 82 (40 ),

The colorless foam was dissolved in diethyl ether and to it was added a saturated solution of maleic acid in diethyl ether. The resultant solid was washed several times with diethyl ether and was then recrystallized to give 0.341 gm of the title compound as an off-white solid, m.p.=177°–179° C. dec. (methanol/ethyl acetate).

Analysis, calculated for C$_{17}$H$_{24}$N$_2$O·2C$_4$H$_4$O$_4$: Theory: C, 59.52; H, 6.39; N, 5.55. Found: C, 59.77; H, 6.28; N, 5.37.

EXAMPLE 5

Preparation of cis-hexahydro-2-methyl-5-(1,2,3,4-tetrahydro- 5-bromo-8-methoxy-2-naphthalenyl)pyrrolo<3,4-c>pyrrole dimaleate A solution of 0.12 gm (0.42 mMol) of cis-hexahydro-2-methyl- 5-(1,2,3,4-tetrahydro-8-methoxy-2-naphthalenyl)pyrrolo< 3,4-c>pyrrole in 5.0 mL trifluoroacetic acid was cooled to 0° C. and then 75 mg (0.42 mMol) of N-bromosuccinimide were added. The reaction mixture was stirred at ambient temperature for 18 hours.

The reaction mixture was then poured into ice, made basic with concentrated ammonium hydroxide and extracted with dichloromethane. The organic phase was dried over sodium sulfate and then concentrated in vacuo to give a yellow glass. The glass was dissolved in dichloromethane and then placed on a flash silica gel column. The column was eluted with 97:3 dichloromethane:methanol containing a trace of ammonium hydroxide. Fractions containing the desired compound were combined and concentrated in vacuo to give 0.13 gm of a colorless glass.

The colorless glass was dissolved in ethanol to which were added 2 equivalents of maleic acid. The solution was heated to reflux for five minutes and was then allowed to cool to ambient. The resultant solid was recrystallized to give 0.12 gm of the title compound as colorless crystals, m.p. =188°–189° C.

NMR(CDCl$_3$): 7.2 (d, J=9 Hz, 1H), 6.5 (d, J=9 Hz, 1H), 3.7 (s, 3H), 3.1–1.9 (m, 17H), 2.3 (s, 3H).

MS: 366(12), 364(14), 322(14), 320(16), 160(35), 125(40), 115(28), 96(100), 82(65), 58(87).

Analysis, calculated for C$_{18}$H$_{25}$N$_2$OBr·2C$_4$H$_4$O$_4$: Theory: C, 52.27; H, 5.57; N, 4.69. Found: C, 51.99; H, 5.36; N, 4.47.

EXAMPLE 6

Preparation of cis-hexahydro-2-benzyl-5-(1,2,3,4-tetrahydro- 8-methoxy-2-naphthalenyl)pyrrolo<3,4-c>pyrrole dimaleate To a solution of 0.53 gm (3.0 mMol) of 8-methoxy-2-tetralone in 20 mL of toluene were added 0.50 gm (2.48 mMol) cis-hexahydro-2-benzylpyrrolo<3,4-c>pyrrole followed by 0.47 gm (2.48 mMol) p-toluenesulfonic acid monohydrate. The reaction mixture was then stirred at reflux under nitrogen with azeotropic removal of water. After 4 hours the reaction mixture was cooled to ambient and then concentrated in vacuo to give a yellow solid.

To a solution of this yellow solid in 25 mL of ethanol were added in portions 0.40 gm (10.5 mMol) sodium borohydride and the reaction mixture was stirred at ambient temperature for 18 hours. The reaction mixture was then diluted with 10% hydrochloric acid and extracted once with diethyl ether. The phases were separated and the aqueous phase was made basic with concentrated ammonium hydroxide. This aqueous phase was extracted with dichloromethane and the organic phase dried over sodium sulfate then concentrated in vacuo to a brown oil. The oil was dissolved in dichloromethane and placed on a flash silica column. The column was eluted with 97:3 dichloromethane:methanol containing a trace of ammonium hydroxide. Fractions containing the desired compound were combined and concentrated in vacuo to give 0.51 gm of a tan oil.

A 0.10 gm portion of this oil was dissolved in about 10 mL of hot ethanol and to it was added a solution of 0.08 gm of maleic acid in hot ethanol. The reaction mixture was heated to reflux for about 5 minutes and was then allowed to cool to ambient. The title compound was recovered as 0.15 gm of colorless crystals, m.p.=196°–198° C. (ethanol).

NMR(CDCl$_3$): 7.2 (m, 5H), 7.0 (t, J=9 Hz, 1H), 6.7–6.5 (m, 2H), 3.8 (s, 3H), 3.6 (s, 2H), 3.2–2.3 (m, 14H), 2.3–1.9 (m, 3H).

MS: 362(15), 271(67), 242(11), 228(5), 201(7), 161(71), 134(10), 91(100), 72(26), 55(48).

Analysis, calculated for C$_{24}$H$_{30}$N$_2$O·2C$_4$H$_4$O$_4$: Theory: C, 64.63; H, 6.44; N, 4.71. Found: C, 64.76; H, 6.48; N, 4.58.

EXAMPLE 7

Preparation of cis-hexahydro-5-(1,2,3,4-tetrahydro-8-methoxy- 2-naphthalenyl)pyrrolo<3,4-c>pyrrole dimaleate To a solution of 1.0 gm (2.8 mMol) cis-hexahydro-2-benzyl-5-(1,2,3,4-tetrahydro-8-methoxy-2-naphthalenyl)pyrrolo< 3,4-c>pyrrole in 20 mL of methanol were added 1.0 gm of 10% palladium on carbon followed by 0.95 gm (15.0 mMol) of ammonium formate. The mixture was then heated at reflux under nitrogen for 15 minutes. The reaction mixture was then filtered through a bed of Celite and the filter pad washed with 20 mL of dichloromethane. The combined filtrates were concentrated in vacuo to an orange glass.

The orange glass was dissolved in dichloromethane and placed on a flash silica column. The column was eluted with 95:5 dichloromethane:methanol containing a trace of ammonium hydroxide. Fractions containing the desired product were combined and concentrated in vacuo to give 0.51 gm of a light yellow crystalline solid.

To a solution of 0.20 gm of this crystalline solid in about 10 mL of ethanol were added 2.0 equivalents of maleic acid. The reaction mixture was heated at reflux for about 5 minutes and then allowed to cool to ambient. The title compound was recovered as 0.29 gm of a colorless, crystalline solid, m.p.=158°–160° C. (ethanol).

NMR(CDCl$_3$): 7.0 (t, J=9 Hz, 1 H), 6.7–6.5 (m, 2H), 3.8 (s, 3H), 3.1–2.5 (m, 10 H), 2.5–2.2 (m, 4 H), 2.2–1.9 (m, 4 H).

MS: 272(45), 271(20), 242(43), 228(8), 161(90), 98(57), 82 (64), 55(100/.

Analysis, calculated for $C_{17}H_{24}N_2O \cdot 2C_4H_4O_4$: Theory: C, 59.52; H, 6.39; N, 5.55. Found: C, 59.53; H, 6.29; N, 5.41.

EXAMPLE 8

Preparation of cis-hexahydro-5-(1,2,3,4-tetrahydro-5-bromo-8-methoxy- 2-naphthalenyl)pyrrolo<3,4-c>pyrrole dimaleate Using 0.31 gm (1.14 mMol) of cis-hexahydro-5-(1,2,3,4-tetrahydro- 8-methoxy-2-naphthalenyl)pyrrolo<3,4-c>pyrrole dimaleate in the method described in Example 5, the title compound was obtained as 0.36 gm of colorless crystals, m.p.= 168° C. (ethanol).

NMR (CDCl$_3$ ): 7.2 (d, J=9 Hz, 1H), 6.4 (d, J=9 Hz, 1H), 3.7 (s, 3H), 3.2–2.5 (m, 10H), 2.5–1.9 (m, 8H).

MS: 352(14), 350(10), 322(17), 320(18), 240(10), 160(12), 98(42), 72(48), 46(100).

Analysis, calculated for $C_{17}H_{23}N_2OBr \cdot 2C_4H_4O_4$: Theory: C, 51.47; H, 5.36; N, 4.80. Found: C, 51.23; H, 5.27; N, 4.88.

Employing the method described in detail in Examples 2 and 5, the compounds of Examples 9 and 10 were prepared.

EXAMPLE 9

Preparation of cis-hexahydro-2-methyl-5-(1,2,3,4-tetrahydro- 8-methyl-2-naphthalenyl)pyrrolo<3,4-c>pyrrole dimaleate Using 0.70 gm 8-methyl-2-tetralone and 0.83 gm cis-hexahydro- 2-methylpyrrolo<3,4-c>pyrrole, 0.13 gm of the title compound were recovered as colorless crystals, m.p.= 197°–198° C. (ethanol).

NMR(CDCl$_3$): 6.9 (s, 3H), 3.1–2.9 (m, 2H), 2.9–2.6 (m, 6H), 2.6–1.9 (m, 9H), 2.3 (s, 3H), 2.2 (s, 3H).

MS: 271(8), 270(39), 226(28), 200(11), 173(13), 145(12), 125(28), 115(21), 96(91), 82(59), 58(80), 55(100).

Analysis, calculated for $C_{18}H_{26}N_2O \cdot 2C_4H_4O_4$: Theory: C, 62.14; H, 6.82; N, 5.57. Found: C, 62.35; H, 7.02; N, 5.80.

EXAMPLE 10

Preparation of cis-hexahydro-2-methyl-5-(1,2,3,4-tetrahydro- 5-bromo-8-methyl-2-naphthalenyl)pyrrolo<3,4-c>pyrrole dimaleate Using 0.53 gm cis-hexahydro-2-methyl-5-(1,2,3,4-tetrahydro- 8-methyl-2-naphthalenyl)pyrrolo<3,4-c>pyrrole, 0.56 gm of the title compound were recovered as colorless crystals, m.p.=191.5°–192° C. (ethanol).

NMR(CDCl$_3$): 7.2 (d, J=9 Hz, 1H), 6.7 (d, J=9 Hz, 1H), 3.1– 1.9 (m, 17H), 2.3 (s, 3H), 2.1 (s, 3H).

MS: 350(17), 348(15), 306(14), 304(14), 144(27), 125(28), 96(100), 82(46), 58(53).

Analysis, calculated for $C_{18}H_{25}N_2OBr \cdot 2C_4H_4O_4$: Theory: C, 53.71; H, 5.72; N, 4.82. Found: C, 53.95; H, 5.70; N, 4.57.

EXAMPLE 11

Preparation of cis-hexahydro-2-methyl-5-(cis-1-methyl-1,2,3,4-tetrahydro-8-methoxy-2-naphthalenyl)pyrrolo< 3,4-c>pyrrole dimaleate A. 1-Methyl-8-methoxy-2-tetralone To 75 mL of toluene were added 3.52 gm (20 mMol) of 8-methoxy- 2-tetralone followed by 2.5 gm of pyrrolidine. The mixture was heated to reflux for 3 hours after which the solvent was evaporated in vacuo to give 3-pyrrolidino-5-methoxy- 1,2-dihydronaphthalene as a dark oil.

The oil was dissolved in 25 mL of p-dioxane. To the solution then were added 7.5 mL of methyl iodide and the mixture was stirred for 18 hours at reflux under nitrogen. The mixture then was diluted with 25 mL of water and 1 mL of glacial acetic acid, after which it was stirred at reflux for 3 hours. The mixture then was cooled to room temperature and the volatiles removed in vacuo. The resulting residue was suspended in water and then extracted with diethyl ether. The organic extracts were combined, washed with saturated aqueous sodium chloride, dried over sodium sulfate and concentrated in vacuo to give 3.5 gm of a dark oil. The oil was dissolved in 1:1 hexane:diethyl ether and placed on a flash silica column. The column was eluted with 1:1 hexane:diethyl ether and fractions found to contain the title compound were concentrated in vacuo to give 3.27 gm (86.5%) of a light brown, transparent oil.

B. cis-hexahydro-2-methyl-5-(cis-1-methyl-1,2,3,4-tetrahydro- 8-methoxy-2-naphthalenyl)pyrrolo< 3,4-c>pyrrole dimaleate Using 0.64 gm 1-methyl-8-methoxy-2-tetralone and 0.65 gm cis-hexahydro-2-methylpyrrolo<3,4-c>pyrrole in the method described in Example 6, 0.04 gm of the title compound were obtained as a white powder, m.p.= 173°–175° C. (ethanol).

NMR (CDCl$_3$ ): 7.0 (t, J=9 Hz, 1H) , 6.8–6.5 (m, 2H), 3.7 (s, 3H), 3.5–2.9 (m, 2H), 2.9–2.0 (m, 8H), 2.3 (s, 3H), 2.0–1.6 (m, 2H), 1.1 (d, J=8 Hz, 3H) .

MS: 301(13), 300(42), 285(5), 256 (33) , 230 (17) , 218 (5) , 203(21), 175(81), 159(14), 125(33), 96(48), 75(16), 60(100).

Analysis, calculated for $C_{19}H_{28}N_2O \cdot 2C_4H_4O_4$: Theory: C, 60.89; H, 6.81; N, 5.26. Found: C, 60.66; H, 6.66; N, 5.07.

EXAMPLE 12 cis-hexahydro-5-(cis-1-methyl-1,2,3,4-tetrahydro-8-methoxy-2-naphthalenyl)pyrrolo< 3,4-c>pyrrole dimaleate Using 2.5 gm 1-methyl-8-methoxy-2-tetralone and 2.43 gm cis-hexahydro-2-benzyl-pyrrolo<3,4-c>pyrrole in the method described in Examples 6 and 7, 0.11 gm of the title compound were obtained as a white solid, 148°–149° C. (ethanol).

NMR(CDCl$_3$): 7.0 (t, J=9 Hz, 1H) , 6.8–6.5 (m, 2H), 3.7 (s, 3H), 3.4–3.0 (m, 2H) , 3.0–2.2 (m, 12H), 2.2–1.6 (m, 3H), 1.1 (d, J=8 Hz, 3H).

MS: 287(15), 286(61), 285(41), 256(67), 242(16), 203(18), 175(100), 159(26), 133(41), 98(85), 82(47), 72(40), 55(99).

Analysis, calculated for $C_{18}H_{26}N_2O \cdot 2C_4H_4O_4$: Theory: C, 60.22; H, 6.61; N, 5.40. Found: C, 60.52; H, 6.71; N, 5.48.

As previously discussed, the compounds of this invention are useful for selectively inhibiting the reuptake of serotonin. Therefore, another embodiment of this invention is a method for inhibiting serotonin reuptake in mammals which comprises administering to a mammal requiring increased serotonin neurotransmission a pharmaceutically effective amount of the invention.

The term "pharmaceutically effective amount", as used herein, represents an amount of a compound of the invention which is capable of inhibiting serotonin reuptake. The specific dose of compound administered according to this invention will be determined by the particular circumstances surrounding the case including, for example, the compound administered, the route of administration and the condition being treated. A typical dose will generally be in the range of about 0.01 mg/kg to about 20 mg/kg of the active compound of this invention. Preferred daily doses will generally be in the range of about 0.05 mg/kg to about 10 mg/kg, and ideally from about 0.1 mg/kg to 5 mg/kg.

The compounds of this invention can be administered by a variety of routes including oral, rectal, transdermal, subcutaneous, intravenous, intramuscular and intranasal. A special feature of the compounds of this invention is that they are selective as inhibitors of serotonin reuptake relative to other monoamines.

A variety of physiologic functions have been shown to be subject to influence by brain serotonergic neural systems. As such, the compounds of this invention are believed to have the ability to treat in mammals a variety of disorders associated with these neural systems such as eating disorders, depression, alcoholism, pain, loss of memory and anxiety. Therefore, the present invention also provides methods of treating the above disorders at rates set forth above for inhibiting serotonin reuptake in mammals.

The following experiment was conducted to demonstrate the ability of the compounds of the present invention to inhibit the reuptake of serotonin. This general procedure is described in Wong et al., *Drug Development Research*, 6, 397– 403 (1985).

Male Sprague-Dawley rats (110–150 gm) from Harlan Industries (Cumberland, Ind.) were fed Purina Chow ad libitum for at least three days before being used in the study. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal reuptake of $^3$H-serotonin ($^3$H-5-hydroxytryptamine, $^3$H-5HT) was determined as follows: Cortical synaptosomes (equivalent to 1 mg protein) were incubated at 37° C. for 5 min. in 1 mL of Krebs-bicarbonate medium containing also 10 mM glucose, 0.1 mM iproniazide, 1 mM ascorbic acid, 0.17 mM EDTA and 50 nM $^3$H-5HT. The reaction mixture was immediately diluted with 2 mL of ice chilled Krebs-bicarbonate buffer and filtered under vacuum with a cell harvester (Brandel, Gaithersburg, Md.). Filters were rinsed twice with approximately 5 mL ice chilled 0.9% saline and were transferred to a counting vial containing 10 mL of scintillation fluid (PCS, Amersham, Arlington Heights, Ill.). Radioactivity was measured by a liquid scintillation spectrophotometer. Accumulation of $^3$H-5HT at 4° C. represented the background and was subtracted from all samples.

The results of the evaluation of various compounds of the present invention are set forth below in Table I. In Table I, the first column provides the Example Number of the compound evaluated; the next 4 columns identify the structure of the compound evaluated when taken with the formula set forth in the heading and the final column provides the amount of the test compound expressed in nanomolar concentration needed to inhibit the uptake of $^3$H-SHT by 50% and is indicated in Table I as $IC_{50}$.

TABLE I

| Compound of Example Number | R | $R^1$ | $R^2$ | $R^3$ | $R^4$ | $R^5$ | $IC_{50}$(nM) 5HT |
|---|---|---|---|---|---|---|---|
| 1 | $CH_3$ | H | H | H | H | H | 122.0 |
| 2 | $CH_3$ | H | Cl | H | H | H | 42.0 |
| 3 | $CH_3$ | H | $OCH_3$ | H | H | H | 20.0 |
| 4 | $CH_3$ | H | OH | H | H | H | 5.4 |
| 5 | $CH_3$ | H | $OCH_3$ | H | H | Br | 38.0 |
| 6 | $CH_2Ph$ | H | $OCH_3$ | H | H | H | 60.0 |
| 7 | H | H | $OCH_3$ | H | H | H | 30.0 |
| 8 | H | H | $OCH_3$ | H | H | Br | 50.0 |
| 9 | $CH_3$ | H | $CH_3$ | H | H | H | 293.0 |
| 10 | $CH_3$ | H | $CH_3$ | H | H | Br | 413.0 |
| 11 | $CH_3$ | Me | $OCH_3$ | H | H | H | 65.0 |
| 12 | H | Me | $OCH_3$ | H | H | H | 340.0 |

The compounds of this invention are preferably formulated prior to administration. Therefore, another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatine capsules, suppositories, sterile injectable solutions, sterile packaged powders and the like.

Examples of suitable carriers, excipients and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl hydroxybenzoates, propyl hydroxybenzoates, talc, magnesium stearate and mineral oil. The formulations may additionally include lubricating agents, wetting agents, emulsifying agents, suspending agents, preserving agents, sweetening agents, flavoring agents and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION I

Hard gelatine capsules are prepared using the following ingredients:

|  | Quantity (mg/capsule) |
| --- | --- |
| cis-hexahydro-5-(cis-1-methyl-1,2,3,4-tetrahydro-6-chloro-2-naphthalenyl)pyrrolo<3,4-c>pyrrole | 250 |
| starch, dried | 200 |
| magnesium stearate | 10 |
| TOTAL | 460 |

The above ingredients are mixed and filled into hard gelatine capsules in 460 mg quantities.

FORMULATION II

A tablet is prepared using the ingredients below:

|  | Quantity (mg/tablet) |
| --- | --- |
| cis-hexahydro-5-(cis-1-methyl-1,2,3,4-tetrahydro-2-naphthalenyl)pyrrolo<3,4-c>-pyrrole dihydrochloride | 250 |
| cellulose, microcrystalline | 400 |
| silicon dioxide, fumed | 10 |
| stearic acid | 5 |
| TOTAL | 665 |

The components are blended and compressed to form tablets each weighing 665 mg.

FORMULATION III

An aerosol solution is prepared containing the following components:

|  | Weight % |
| --- | --- |
| cis-hexahydro-5-(1,2,3,4-tetrahydro-6-chloro-2-naphthalenyl)pyrrolo<3,4-c>pyrrole dimaleate | 0.25 |
| ethanol | 29.75 |
| Propellant 22 | |

-continued

|  | Weight % |
| --- | --- |
| (chlorodifluoromethane) | 70.00 |
| TOTAL | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION IV

Tablets, each containing 60 mg of active ingredient are made as follows:

| cis-hexahydro-2-methyl-5-(1,2,3,4-tetrahydro-8-chloro-2-naphthalenyl) pyrrolo-<3,4-c>pyrrole dimaleate | 60.0mg |
| --- | --- |
| starch | 45.0mg |
| microcrystalline cellulose | 35.0mg |
| polyvinylpyrrolidone (as 10% aqueous solution) | 4.0mg |
| sodium carboxymethyl starch | 4.5mg |
| magnesium stearate | 0.5mg |
| talc | 1.0mg |
| TOTAL | 150.0mg |

The active ingredient, starch and cellulose are passed through a No. 45 mesh U.S. sieve and mixed thoroughly. The aqueous solution containing polyvinylpyrrolidone is mixed with the resultant powder, and the mixture is then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION V

Capsules, each containing 80 mg of active ingredient, are made as follows:

| cis-hexahydro-5-(1,2,3,4-tetrahydro-5-bromo-8-methoxy-2-naphthalenyl) pyrrolo-<3,4-c>pyrrole dihydrochloride | 80 mg |
| --- | --- |
| starch | 59 mg |
| microcrystalline cellulose | 59 mg |
| magnesium stearate | 2 mg |
| TOTAL | 200 mg |

The active ingredient, cellulose, starch and magnesium stearate are blended, passed through a No. 45 mesh U.S. sieve, and filled into hard gelatine capsules in 200 mg quantities.

FORMULATION VI

Suppositories, each containing 225 mg of active ingredient, are made as follows:

| | |
|---|---|
| cis-hexahydro-2-methyl-5-(1,2,3,4-tetrahydro-5-bromo-8-methoxy-2-naphthalenyl) pyrrolo<3,4-c>pyrrole dihydrochloride hydrate | 225 mg |
| saturated fatty acid glycerides | 2,000 mg |
| TOTAL | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 gm capacity and allowed to cool.

FORMULATION VII

Suspensions, each containing 50 mg of active ingredients per 5 mL dose, are made as follows:

| | |
|---|---|
| cis-hexahydro-2-methyl-5-(1,2,3,4-tetrahydro-5-cyano-8-methoxy-2-naphthalenyl) pyrrolo<3,4-c>pyrrole dihydrochloride | 50.0 mg |
| sodium carboxymethyl cellulose | 50.0 mg |
| syrup | 1.25mL |
| benzoic acid solution | 0.10mL |
| flavor | q.v. |
| color | q.v. |
| purified water to total | 5.0 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added with stirring. Sufficient water is then added to produce the required volume.

FORMULATION VIII

An intravenous formulation may be prepared as follows:

| | |
|---|---|
| cis-hexahydro-2-methyl-5-(1,2,3,4-tetrahydro-8-hydroxy-2-naphthalenyl) pyrrolo<3,4-c>pyrrole dihydrobromide | 100 mg |
| isotonic saline | 1000 L |

The solution of the above ingredients generally is administered at a rate of 1 mL per minute to a subject suffering from depression.

We claim:

1. A compound of the formula

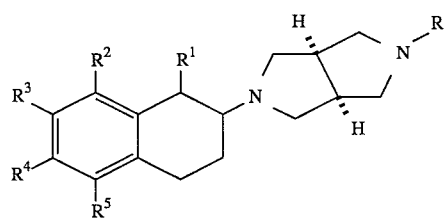

in which

R is hydrogen, methyl or benzyl;

$R^1$ is hydrogen or methyl;

$R^2$ is selected from the group consisting of hydrogen, halo, $C_1$–$C_3$ alkoxy, $C_1$–$C_3$ alkylthio, $C_1$–$C_3$ alkyl and hydroxy;

$R^3$ is selected from the group consisting of hydrogen and halo;

$R^4$ is selected from the group consisting of hydrogen, halo, $C_1$–$C_3$ alkoxy, $C_1$–$C_3$ alkylthio, $C_1$–$C_3$ alkyl and hydroxy;

$R^5$ is selected from the group consisting of hydrogen, halo, $C_1$–$C_3$ alkyl, $C_1$–$C_3$ alkoxy, $C_1$–$C_3$ acyl, fluorosubstituted $C_2$–$C_3$ acyl, fluorosubstituted $C_1$–$C_3$ alkyl, cyano, carboxamido, carboxyl and $C_1$–$C_3$ hydroxyalkyl; all subject to the following provisos:

(a) $R^5$ is other than hydrogen only when $R^2$ is other than hydrogen;

(b) $R^3$ is halo only when $R^4$ is other than hydrogen; or a pharmaceutically acceptable acid addition salt thereof.

2. A compound of claim 1, in which $R^5$ is selected from the group consisting of hydrogen, halo, $C_1$–$C_3$ alkyl, $C_1$–$C_3$ acyl, fluorosubstituted $C_2$–$C_3$ acyl, fluorosubstituted $C_1$–$C_3$ alkyl and cyano.

3. A compound of claim 2, in which $R^2$ is selected from the group consisting of halo, $C_1$–$C_3$ alkoxy, $C_1$–$C_3$ alkylthio, $C_1$–$C_3$ alkyl and hydroxy.

4. A compound of claim 3, in which $R^1$ is hydrogen.

5. A compound of claim 4, in which R is methyl.

6. A compound of claim 4, in which $R^2$ is $C_1$–$C_3$ alkoxy or halo.

7. A compound of claim 6, in which $R^2$ is halo.

8. A compound of claim 7, in which $R^2$ is chloro.

9. A compound of claim 6, in which $R^2$ is $C_1$–$C_3$ alkoxy.

10. A compound of claim 9, in which $R^2$ is methoxy.

11. A compound of claim 9, in which $R^5$ is halo.

12. A compound of claim 9, in which $R^5$ is bromo.

13. A compound of claim 2, in which $R^4$ is selected from the group consisting of halo, $C_1$–$C_3$ alkyl and $C_1$–$C_3$ alkylthio.

14. A compound of claim 13, in which $R^1$ is methyl.

15. A compound of claim 14, in which R is hydrogen.

16. A compound of claim 15, in which $R^4$ is halo.

17. A compound of claim 16, in which $R^4$ is chloro.

18. A compound of claim 17 in which $R^3$ is hydrogen.

19. A method for inhibiting serotonin reuptake in mammals which comprises administering to a mammal requiring increased neurotransmission of serotonin a pharmaceutically effective amount of a compound of the formula

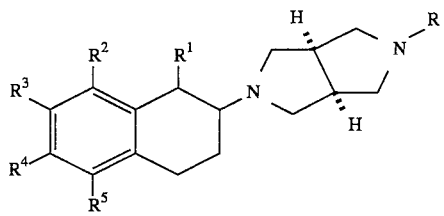
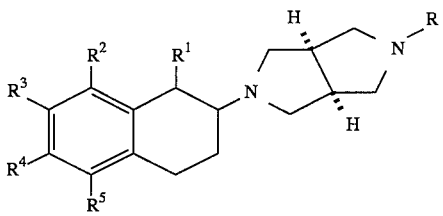

in which

R is hydrogen, methyl or benzyl;

$R^1$ is hydrogen or methyl;

$R^2$ is selected from the group consisting of hydrogen, halo, $C_1$–$C_3$ alkoxy, $C_1$–$C_3$ alkylthio, $C_1$–$C_3$ alkyl and hydroxy;

$R^3$ is selected from the group consisting of hydrogen and halo;

$R^4$ is selected from the group consisting of hydrogen, halo, $C_1$–$C_3$ alkoxy, $C_1$–$C_3$ alkylthio, $C_1$–$C_3$ alkyl and hydroxy;

$R^5$ is selected from the group consisting of hydrogen, halo, $C_1$–$C_3$ alkyl, $C_1$–$C_3$ alkoxy, $C_1$–$C_3$ acyl, fluoro-substituted $C_2$–$C_3$ acyl, fluorosubstituted $C_1$–$C_3$ alkyl, cyano, carboxamido, carboxyl and $C_1$–$C_3$ hydroxyalkyl; all subject to the following provisos:

(a) $R^5$ is other than hydrogen only when $R^2$ is other than hydrogen;

(b) $R^3$ is halo only when $R^4$ is other than hydrogen;

or a pharmaceutically acceptable acid addition salt thereof.

20. A method of claim 19, in which the compound is cis-hexahydro- 2-methyl-5-(1,2,3,4-tetrahydro-8-methoxy-2-naphthalenyl)pyrrolo< 3,4-c>pyrrole.

21. A pharmaceutical formulation which comprises, in association with a pharmaceutically acceptable carrier, diluent or excipient, a compound of the formula in which R is hydrogen, methyl or benzyl;

$R^1$ is hydrogen or methyl;

$R^2$ is selected from the group consisting of hydrogen, halo, $C_1$–$C_3$ alkoxy, $C_1$–$C_3$ alkylthio, $C_1$–$C_3$ alkyl and hydroxy;

$R^3$ is selected from the group consisting of hydrogen and halo;

$R^4$ is selected from the group consisting of hydrogen, halo, $C_1$–$C_3$ alkoxy, $C_1$–$C_3$ alkylthio, $C_1$–$C_3$ alkyl and hydroxy;

$R^5$ is selected from the group consisting of hydrogen, halo, $C_1$–$C_3$ alkyl, $C_1$–$C_3$ alkoxy, $C_1$–$C_3$ acyl, fluorosubstituted $C_2$–$C_3$ acyl, fluorosubstituted $C_1$–$C_3$ alkyl, cyano, carboxamido, carboxyl and $C_1$–$C_3$ hydroxyalkyl; all subject to the following provisos:

(a) $R^5$ is other than hydrogen only when $R^2$ is other than hydrogen;

(b) $R^3$ is halo only when $R^4$ is other than hydrogen;

or a pharmaceutically acceptable acid addition salt thereof.

22. A formulation of claim 21, in which the compound is cis-hexahydro-2-methyl-5-(1,2,3,4-tetrahydro-8-methoxy-2-naphthalenyl)pyrrolo< 3,4-c>pyrrole.

\* \* \* \* \*